Sept. 18, 1962 H. M. TIRET Plant Pat. 2,171
FUCHSIA PLANT
Filed Oct. 27, 1961
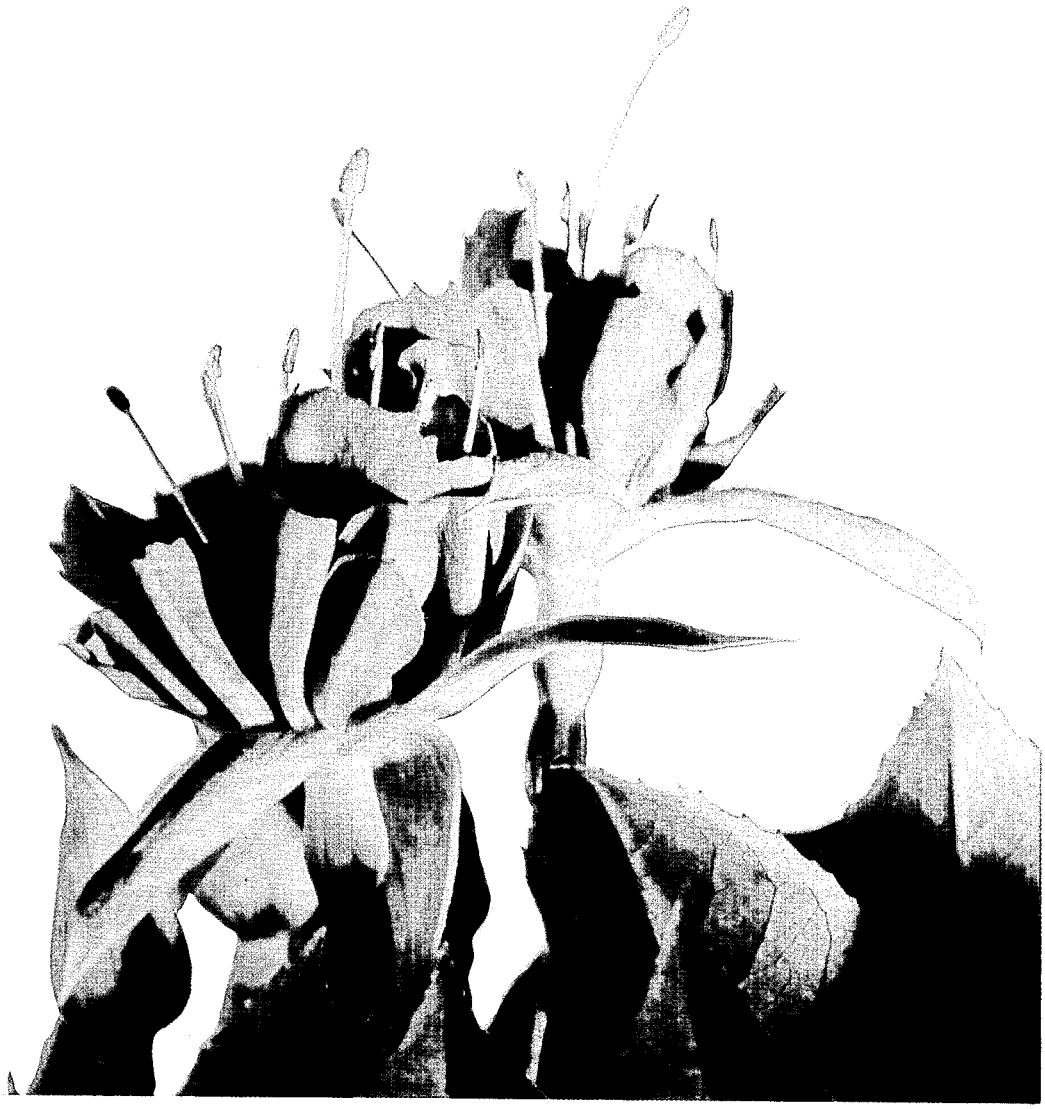

United States Patent Office

Plant Pat. 2,171
Patented Sept. 18, 1962

2,171
FUCHSIA PLANT

Horace M. Tiret, 2126 Taraval St., San Francisco, Calif.

Filed Oct. 27, 1961, Ser. No. 148,301
1 Claim. (Cl. 47—60)

This invention relates to a new and improved fuchsia plant, the principal new and different characteristic of which is the unusual color Fuchsine Pink petals (British Horticultural Chart #627) combined with a classical symmetrical form, unlike any other fuchsia plant.

The accompanying drawing illustrates the plant in bloom and the aforementioned new and different characteristics.

The fuchsia plant was derived as a hybrid from seedlings (unpatented) not introduced to the trade, namely 11/31/1 and 12/54/10 (figures representing applicant's own breeding symbols). The plant has been asexually reproduced at Colma, California, by cuttings which retained the characteristics of the parent fuchsia plant.

The plant is a vigorous, semi-trailing variety. It is a heavy early bloomer.

In the accompanying drawing, the FIGURE shows a typical branch tip represented in approximate actual size.

A detailed description of the new variety of fuchsia plant follows (all measurements approximate):

*Habit of growth.*—Vigorous, semi-trailing variety. Early crop bloomer. The flowers are produced in abundance.

*Foliage.*—The leaves are dark green, medium in size, medium veined surface. The mature leaf is approximately 3″ in length and 1⅞″ in width at the broadest point. Texture of the leaf, crinkly (medium). Branches are greenish-brown.

*Buds.*—Color of buds is Neyron Rose (British Horticultural Color Chart #623). Buds are variegated, ranging in color from 623/3 to 623 with distinctive green tips. Length from ovary is approximately 2½″. Width at broadest point is 1″.

*Ovary.*—Color of the ovary is green. Length is ½″. Width at broadest point, at maturity, is 5/16″.

*Sepals.*—There are 4 sepals, each 2″ in length and ⅝″ in width at the broadest point. Form is slender and recurved. The texture at the underside is slightly crepe and the outer surface is smooth. Color of the underside is Neyron Rose. (British Horticultural Color Chart #623/1) with green tips. The outside color is Neyron Rose, #623/3.

*Tube.*—Medium and slender. Length is ⅝″, width 5/16″ at broadest point. Color, Neyron Rose, #623/3.

*Stamens.*—There are 8 stamens, colored rose, with rose anthers. Form is medium slender, length is 2″.

*Pistil.*—The style is 3″ in length, 1/32″ in width. The color is flesh, the stigma flesh color.

*Petals.*—Color of all petals is Fuchsine Pink (British Horticultural Color Chart #627).

The petals are 22 in number. They are large with fully open flaring corolla. The diameter of the fully open mature flower is 3″. The large petals are 1⅜″ in length and 1¼″ in width. The texture is smooth.

*Parentage.*—Applicant's own seedlings, not introduced to the trade, unpatented, namely, 11/31/1 and 12/54/10. (Figures represent applicant's own breeding symbols.)

Having thus disclosed my discovery, I claim:

A new and distinct variety of fuchsia plant, substantially asherein shown and described, characterized by the unusual Fuchsine Pink coloring of the entire corolla in combination with its exceptional flaring form, which fuchsia plant is very vigorous and semi-trailing in habit of growth.

No references cited.